United States Patent
Rau

(10) Patent No.: US 8,956,652 B2
(45) Date of Patent: Feb. 17, 2015

(54) EFFERVESCENT REHYDRATING BEVERAGE TABLET/GRANULES

(75) Inventor: Allen H. Rau, Cincinnati, OH (US)

(73) Assignee: Tower Laboratories, Ltd., Centerbrook, CT (US)

( * ) Notice: Subject to any disclaimer, the term of this patent is extended or adjusted under 35 U.S.C. 154(b) by 2172 days.

(21) Appl. No.: 11/226,415

(22) Filed: Sep. 15, 2005

(65) Prior Publication Data

US 2007/0059362 A1 Mar. 15, 2007

(51) Int. Cl.

| | |
|---|---|
| *A61K 9/46* | (2006.01) |
| *A23L 2/395* | (2006.01) |
| *A23L 2/40* | (2006.01) |
| *A23L 2/52* | (2006.01) |
| *A61K 31/19* | (2006.01) |
| *A61K 33/00* | (2006.01) |
| *A61K 33/04* | (2006.01) |
| *A61K 33/06* | (2006.01) |
| *A61K 33/10* | (2006.01) |
| *A61K 33/32* | (2006.01) |
| *A61K 45/06* | (2006.01) |

(52) U.S. Cl.
CPC ............... *A61K 9/0007* (2013.01); *A23L 2/395* (2013.01); *A23L 2/40* (2013.01); *A23L 2/52* (2013.01); *A61K 31/19* (2013.01); *A61K 33/00* (2013.01); *A61K 33/04* (2013.01); *A61K 33/06* (2013.01); *A61K 33/10* (2013.01); *A61K 33/32* (2013.01); *A61K 45/06* (2013.01)
USPC .......................................... 424/466; 424/680

(58) Field of Classification Search
None
See application file for complete search history.

(56) References Cited

U.S. PATENT DOCUMENTS

| | | |
|---|---|---|
| 3,337,404 A | 8/1967 | Polli et al. |
| 4,874,606 A | 10/1989 | Boyle et al. |
| 5,114,723 A | 5/1992 | Stray-Gundersen |
| 5,164,192 A | 11/1992 | Louwes |
| 5,397,786 A | 3/1995 | Simone |
| 5,447,730 A | 9/1995 | Greenleaf |
| 6,329,414 B1 | 12/2001 | Thomas et al. |
| 2003/0134804 A1 | 7/2003 | King et al. |
| 2005/0048136 A1 | 3/2005 | Choudhry |

*Primary Examiner* — Hasan Ahmed
(74) *Attorney, Agent, or Firm* — Steven B. Kelber

(57) ABSTRACT

Effervescent tablets, powders and granules are provided which may be dissolved in water to produce an effervescent rehydrating beverage. The effervescent tablet, powder and granule compositions of the invention deliver electrolytes and carbohydrates at levels that provide hypotonic, isotonic or slightly hypertonic solution when dissolved in water, with acceptable taste.

20 Claims, No Drawings

EFFERVESCENT REHYDRATING BEVERAGE TABLET/GRANULES

BACKGROUND

Beverages that are designed to rehydrate the body are well known. These products provide electrolytes and carbohydrates in proportions and levels that are easily adsorbed by the body. They can be designed for use during strenuous physical exertion, relief of dehydration caused by nausea and/or diarrhea, or for efficient delivery of vitamins, minerals and/or drugs. Some ready-to-drink (RTD) products that deliver these benefits include Gatorade®, Powerade®, and Pedialyte®.

One of the keys to delivering these benefits is to assure that the beverage has the proper osmolality. Osmolality is a measure of the number of dissolved particles in a solution. Normal body fluids have a natural osmolality of about 280-302 mOsm/kg. Beverages that have lower osmolality than this are considered hypotonic; those with osmolality in this range are isotonic; those with greater osmolality are hypertonic. In general, hypotonic and isotonic products provide the best rehydration benefits. Slightly hypertonic products may also be acceptable.

Beyond the osmolality of the product, the amount of electrolyte and carbohydrate that it provides are also important for delivery of the intended benefit. The World Health Organization (WHO) recommends that Oral Rehydration Salts for treatment of diarrhea deliver the following range of glucose and electrolytes:

Glucose: Not more than 111 mmol/l
Sodium: 60-90 mEq/l
Potassium: 15-25 mEq/l
Citrate: 8-12 mmol/l
Chloride: 50-80 mEq/l
Total substance concentration (including glucose): 200-310 mmol/l
A formulation favored by WHO is:
Sodium Chloride: 2.6 g/l
Glucose, Anhydrous: 13.5 g/l
Potassium Chloride: 1.5 g/l
Trisodium Citrate, Dihydrate: 2.9 g/l
This formula delivers:
Sodium: 75 mmol/l
Chloride: 65 mmol/l
Glucose, Anhydrous: 75 mmol/l
Potassium: 20 mmol/l
Citrate: 10 mmol/l
Total Osmolality: 245 mOsm/kg The WHO recommended product is intended to be delivered as a powder that is dissolved in water just prior to use. WHO acknowledges that this composition can be delivered in liquid or tablet form, but notes that these forms may not be as economical to produce or distribute as powders.

Effervescent rehydration tablets that are designed to dissolve in water to form beverages have been marketed. Servidrat® and Servidrat LS® from Novartis are available in Latin America and other parts of the world. They are used primarily in areas where disease is endemic or where natural disasters have occurred. They are unflavored products that result in salty solutions. They would not be acceptable for commercial sale as consumer products.

It is noteworthy that the WHO acknowledges that color and flavor can be added to Oral Rehydration Salts in order to increase consumer acceptability. However, they reference studies conducted in Egypt and the Philippines that indicate no advantages or disadvantages with regards to safety, acceptability and correct use for flavored/colored product.

Electrolytes are essential to formulating an effective rehydration drink. As shown in the WHO formula above, these materials are generally incorporated as chloride salts. Naturally, these chloride compounds taste salty. This can present a challenge to those attempting to formulate an acceptable tasting product.

From a chemist's point of view, electrolytes are materials that ionize in solution, thus allowing electricity to be conducted. Many organic and inorganic materials meet this requirement. From a physiologist's view point, the important electrolytes are limited to sodium, potassium, chlorine, magnesium, calcium and bicarbonate. For purposes of this invention, electrolytes will be defined as the ionic forms of sodium, potassium, magnesium, calcium, bicarbonate and chlorine. Ions of edible acids such as citrate, tartrate, malate and fumarate are also included as electrolytes.

Carbohydrates are usually included in rehydration drinks. Glucose is known to accelerate the adsorption of both water and dissolved materials in the small intestine. Carbohydrates also contribute to the osmolality of the product and they provide calories that the consumer generally needs. They also tend to add sweetness to the product. This improves consumer acceptability. Glucose, dextrose, and sucrose are the most commonly used carbohydrates. Other carbohydrates include galactose, fructose, lactose and maltose. Maltodextrin and other glucose polymers are also used when the formulator intends that carbohydrate provide a more sustained release of energy (be metabolized more slowly) than it would be with monomer or dimer sugars.

Effervescent tablets that create beverages upon dilution are known. Tablets that deliver vitamins are popular in Europe. Many of these products deliver some level of electrolyte either by design or by the fact that sodium and/or potassium is delivered by the sodium and/or potassium bicarbonate used in the effervescent couple. These products generally do not contain carbohydrates. When carbohydrates are included, they are generally present only at minimal levels. It is hypothesized that these levels are used to improve product performance parameters (such as dissolution rate or sweetness profile) or processability. There would be minimal impact on osmolality.

As noted above, RTD consumer products such as Gatorade®, Powerade®, and Pedialyte® are designed for rehydration benefits. As shown in the table below, these products offer a range of carbohydrate and electrolyte levels (expressed in mmol/liter). Electrolyte and carbohydrate levels for the WHO and Servidrat® products are shown for comparison purposes.

|  | Gatorade ® | Powerade ® | Pedialyte ® | WHO | Servidrat ® | Servidrat LS ® |
|---|---|---|---|---|---|---|
| Sodium | 20 | 10 | 45 | 75 | 90 | 56 |
| Potassium | 3 | 3 | 20 | 20 | 20 | 20 |
| Chloride | 20 | 10 | 35 | 65 | 80 | 46 |
| Bicarbonate | 0 | 0 | 0 | 0 | 30 | 30 |
| Citrate | 0 | 0 | 0 | 10 | 30 | 30 |

-continued

|  | Gatorade® | Powerade® | Pedialyte® | WHO | Servidrat® | Servidrat LS® |
|---|---|---|---|---|---|---|
| Total Electrolyte | 43 | 23 | 100 | 170 | 250 | 182 |
| Dextrose | 330 | 350 | 139 | 75 | 100 | 140 |
| Other Carbohydrate | 0 | 5 | 0 | 0 | 0 | 0 |
| Total Carbohydrate | 330 | 355 | 140 | 75 | 100 | 140 |
| Osmolality (mOm/kg) | 280-360 | 403 | 255 | 245 | 306 | 290 |

It is noteworthy that the RTD sports drinks (Gatorade® and Powerade®) are formulated to give higher carbohydrate levels than the WHO and Servidrat® products. This is not surprising as the sports drinks are designed to boast the user's energy levels by providing readily available calories from simple sugars. It is also interesting to note that all of the commercial products have less electrolyte than the WHO and Servidrat® products. This was probably done to minimize salty taste, making the product more palatable to consumers.

U.S. Pat. No. 3,337,404 teaches effervescent potassium compositions. The compositions comprise potassium bicarbonate, potassium chloride, citric acid, sweeteners and fillers. There is no discussion of how much the water the composition should be dissolved in, so it is not possible to calculate the molar concentration of the various ions. Needless to say, there is no discussion of the osmolality or flavor of the resultant solution.

U.S. Pat. No. 5,114,723 teaches a hypotonic aqueous beverage composition with particular electrolyte and carbohydrate levels. This patent does not lead one skilled in the art to contemplate delivery of these materials in a solid tablet or granule form.

U.S. Pat. No. 5,164,192 relates to specific effervescent compositions for oral rehydration of domestic or companion animals that are suffering from diarrhea. This patent requires the use of lactose and/or amino acids. Thus, this composition would not be useful to persons that are lactose intolerant.

It is the aim of this invention to provide effervescent tablet and granule compositions that deliver electrolytes and carbohydrates at levels that result in hypotonic, isotonic or slightly hypertonic solutions when dissolved in appropriate amounts of water. These formulations are created with electrolyte and carbohydrate levels that are high enough for rehydration but low enough for acceptable taste.

Edible acids and carbonate salts are included in the inventive compositions in order to make them effervescent. Effervescence helps the product dissolve completely and it distributes the components of the product uniformly in the beverage solution. Flavors, sweeteners, and/or colors are included in preferred embodiments. Vitamins, drugs, herbal materials, minerals and other dietary supplements can be added if the formulator desires.

SUMMARY OF THE INVENTION

The present invention is directed to an effervescent tablet, powder or granule comprising an edible acid, a carbonate salt and a carbohydrate. The effervescent tablets, powders or granules of the present invention may further comprise an electrolyte. When diluted in an appropriate amount of water, the effervescent tablet, powder or granule yields a hypotonic, isotonic or slightly hypertonic solution. Preferably, the osmolality of the solution is less than 310 mOsm/kg. Furthermore, the sodium content of the solution preferably does not exceed 52 mmol/liter, and the chloride content of the solution preferably does not exceed 40 mmol/liter.

The effervescent tablet, powder or granule of the present invention is advantageous to prior art effervescent tablets, powder and granules because it provides electrolytes and carbohydrates to the person consuming the solution (in which the tablets, powder or granule have been diluted) at high enough levels to allow for rehydration, but low enough levels to prevent a salty taste to the solution.

DESCRIPTION OF THE INVENTION

The present invention is an effervescent tablet, powder or granule that, when dissolved in an appropriate amount of water, delivers electrolytes and carbohydrates at sufficient concentration to rehydrate the user. This rehydration ability is measured by the dissolved product's osmolality. Further, inventive formulations can be flavored so that they are sufficiently palatable for general consumer use.

Effervescent compositions are characterized by the use of an acid and carbonate salt. When these materials are brought together in the presence of water, they react to yield the salt of the acid, water and gaseous carbon dioxide.

Although any edible acid could be used in this invention, those most likely to be used are citric acid, malic acid, fumaric acid, tartaric acid, succinic acid, ascorbic acid, adipic acid and lactic acid.

The carbonate salts most likely to be used include, sodium bicarbonate, sodium carbonate, sodium sesquicarbonate, potassium carbonate, potassium bicarbonate, potassium sesquicarbonate, magnesium carbonate, calcium carbonate, ammonium bicarbonate, and ammonium sesquicarbonate.

Carbohydrates that can be used in the effervescent tablets, powders or granules of the invention include, but are not limited to, glucose, dextrose, sucrose, galactose, fructose, lactose, maltose and glucose polymers.

It should be noted that additional ingredients chosen for specific benefits can be added to the inventive compositions. Exemplary materials of this type include vitamins (such as vitamin A, the B vitamins, vitamin C, vitamin D, vitamin H, vitamin F, vitamin K, vitamin L, vitamin M and vitamin E), minerals (such as manganese, selenium, calcium, and magnesium), drugs (such as phenylephrine, pseudoephedrine, chlorpheniramine maleate, aspirin, ibuprofen, naproxin, caffeine and acetaminophen) and herbal ingredients (such as ginkgo biloba, echinacea, ginseng, ginger and St. John's wort).

Materials that improve the organoleptic properties of the product can also be included. Examples of this class of material include flavors, colors, artificial sweeteners (such as saccharin, acesulfame-K, sucralose, cyclamate, sucralose, and aspartame), and viscosity modifiers (such as gum arabic, gum acacia, carboxy methyl cellulose and hydroxy propyl methyl cellulose).

If needed, materials that improve the processing of the product can also be added. This class of additive includes lubricants and binders. Lubricants that might be incorporated include polyethylene glycol, magnesium stearate, stearic acid, sucrose stearate, sodium stearyl fumarate, various silicone oils, vegetable oils, mineral oils and sodium benzoate. Binders that might be used include sorbitol, microcrystalline cellulose, dicalcium phosphate, maltodextrin, corn syrup solids, dextrose, sucrose, polyvinyl alcohol, polyvinyl pyrrolidone and sodium sulfate. It is interesting to note that when carbohydrate binders are chosen, they can provide multiple functions to the product—both as the carbohydrate source required by the invention and as the physical binder.

The following tables compare inventive formulations with the formulations discussed above.

TABLE 1

Comparative and Inventive Formulations mg/tablet

| mmol/l | Comparative Examples | | | Inventive Examples | | | |
|---|---|---|---|---|---|---|---|
| | Servidrat ® | LS ® | WHO | 1 | 2 | 3 | 4 |
| Glucose | 2162 | 3027 | 13500 | 2590 | 3382 | 3004 | 3755 |
| Sucrose | 0 | 0 | 0 | 0 | 0 | 3004 | 3755 |
| Glucose polymer (MW: 900) | 0 | 0 | 0 | 445 | 537 | 800 | 0 |
| Glucose polymer (MW: 1800) | 0 | 0 | 0 | 0 | 0 | 0 | 1000 |
| Sodium chloride | 421 | 182 | 2600 | 242 | 277 | 0 | 0 |
| Potassium chloride | 179 | 179 | 1500 | 0 | 0 | 0 | 0 |
| Trisodium citrate dihydrate | 0 | 0 | 2900 | 0 | 0 | 0 | 0 |
| Citric acid | 692 | 692 | 0 | 227 | 260 | 721 | 900 |
| Tartaric acid | 0 | 0 | 0 | 421 | 508 | 0 | 0 |
| Sodium bicarbonate | 295 | 299 | 0 | 97 | 114 | 292 | 365 |
| Potassium bicarbonate | 0 | 0 | 0 | 227 | 270 | 68 | 85 |
| Polyethylene Glycol (MW: 6000) | 0 | 0 | 0 | 0 | 0 | 200 | 200 |
| Sodium benzoate | 0 | 0 | 0 | 0 | 0 | 150 | 150 |
| Sodium saccharin | 0 | 50 | 0 | 0 | 0 | 0 | 0 |
| Acesulfame-K | 0 | 0 | 0 | 16 | 16 | 0 | 0 |
| Flavor | 0 | 0 | 0 | as desired | as desired | as desired | as desired |
| TOTAL mg | 3749 | 4429 | 20500 | 4265+ | 5364+ | 8239+ | 10210+ |
| Effervescence | Yes | Yes | No | Yes | Yes | Yes | Yes |
| ml H$_2$O to dilute | 120 | 120 | 1000 | 120 | 120 | 140 | 140 |

TABLE 2

Comparative and Inventive Formulations mmol/l (diluted per usage instructions)

| mmol/l | Comparative Examples | | | Inventive Examples | | | |
|---|---|---|---|---|---|---|---|
| | Servidrat | LS | WHO | 1 | 2 | 3 | 4 |
| Sodium | 90 | 56 | 75 | 44 | 51 | 32 | 38 |
| Potassium | 20 | 20 | 20 | 20 | 23 | 5 | 6 |
| Chloride | 80 | 46 | 65 | 34 | 39 | 0 | 0 |
| Bicarbonate | 30 | 30 | 0 | 28 | 34 | 30 | 37 |
| Citrate | 30 | 30 | 10 | 10 | 11 | 27 | 33 |
| Tartrate | 0 | 0 | 0 | 23 | 28 | 0 | 0 |
| Glucose | 100 | 140 | 75 | 120 | 157 | 119 | 149 |
| Sucrose | 0 | 0 | 0 | 0 | 0 | 63 | 78 |
| Glucose polymer (MW: 900) | 0 | 0 | 0 | 4 | 5 | 6 | 0 |
| Glucose polymer (MW: 1800) | 0 | 0 | 0 | 0 | 0 | 0 | 4 |
| Osmolality (mOsm/kg) | 306 | 290 | 245 | 269 | 300 | 286 | 304 |
| Saltiness 1-5 scale | 5 | 4 | 3 | 2 | 2 | 1 | 1 |

TABLE 2-continued

Comparative and Inventive Formulations
mmol/l
(diluted per usage instructions)

Comparative Examples

|  | Servidrat | | Inventive Examples | | | |
| --- | --- | --- | --- | --- | --- | --- |
| mmol/l | Servidrat | LS | WHO | 1 | 2 | 3 | 4 |
| 1: No Salt Taste 5: Very Salty | | | | | | | |

Products with saltiness scores of 3, 4, or 5 are considered too salty to effectively mask with well known flavors and/or non-carbohydrate (artificial) sweeteners. Products with scores of 1 or 2 will not be perceived as excessively salty with or without the addition of flavors and/or artificial sweeteners.

Preferably, the osmolality of the diluted effervescent tablets, powders or granules of the present invention is below about 315 mOsm/kg, more preferably below about 310 mOsm/kg, yet more preferably below about 305 mOsm/kg, yet more preferably below about 302 mOsm/kg. In a preferred embodiment, the osmolality of the diluted effervescent tablets, powders or granules is between about 250-302 mOsm/kg, or between about 260-302 mOsm/kg, or between about 270-302 mOsm/kg, or between about 280-302 mOsm/kg, or between about 290-302 mOsm/kg.

An appropriate amount of water for dissolving the tablets, powders or granules of the present invention is an amount sufficient to provide the concentration of carbohydrate, sodium and chloride at a level of 75-125% of that reflected in inventive compositions 1-4, as depicted in tables 1 and 2.

As can be seen from the above tables, the inventive compositions yield beverage solutions that deliver electrolytes and carbohydrates in proportions that result in the proper osmolality for rehydration. Inventively, this is achieved with compositions that are not so salty that they cannot be flavored as consumer acceptable products.

The key to this invention is the design of effervescent systems that, when diluted appropriately, yield hypotonic, isotonic or slightly hypertonic solutions (as defined as having osmolality below about 310 mOsm/kg) in which the sodium content does not exceed 52 mmol/liter and chloride content does not exceed 40 mmol/liter. In other embodiments, the sodium content would not exceed 50, 45, 40, 35 or 30 mmol/liter. In yet other embodiments, the chloride content would not exceed 35 or 30 mmol/liter. Both sodium and chloride content have been attributed to the saltiness of a solution. Further, the solutions made from these compositions are differentiated from conventional effervescent vitamin tablets in that they deliver significant levels of carbohydrate, preferably above 30 mmol/liter, more preferably above 40 mmol/liter, yet more preferably above 50 mmol/liter, and most preferably above 60 mmol/liter.

The exemplary compositions discussed herein are not intended to limit the invention in any way, and one of skill in the art would be aware of other components that could be used in a composition of the present invention, as well as other osmolalities, sodium contents, chloride contents, carbohydrate contents, etc.

What is claimed is:

1. An effervescent tablet, powder or granule comprising: an edible acid; a carbonate salt; and a carbohydrate; wherein said effervescent tablet, powder or granule, when diluted in an appropriate amount of water, yields a solution with an osmolality of less than 310 mOsm/kg in which the sodium and chloride content do not exceed 52 and 40 mmol/liter respectively, and wherein the levels of carbohydrate are above 50 mmol/liter.

2. The effervescent tablet, powder or granule of claim 1, wherein said edible acid is selected from the group consisting of citric acid, malic acid, fumaric acid, tartaric acid, succinic acid, ascorbic acid, adipic acid and lactic acid.

3. The effervescent tablet, powder or granule of claim 1, wherein said carbonate salt is selected from the group consisting of sodium bicarbonate, sodium carbonate, sodium sesquicarbonate, potassium carbonate, potassium bicarbonate, potassium sesquicarbonate, magnesium carbonate, calcium carbonate, ammonium bicarbonate, and ammonium sesquicarbonate.

4. The effervescent tablet, powder or granule of claim 1, wherein said carbohydrate is selected from the group consisting of glucose, dextrose, sucrose, galactose, fructose, lactose, maltose and glucose polymers.

5. The effervescent tablet, powder or granule of claim 1 further comprising dietary supplements selected from the group consisting of one or more vitamins, one or more minerals, one or more drugs, one or more herbal ingredients, and combinations thereof.

6. The effervescent tablet, powder or granule of claim 5, wherein said one or more vitamins is selected from the group consisting of vitamin A, the B vitamins, vitamin C, vitamin D, vitamin H, vitamin F, vitamin K, vitamin L, vitamin M and vitamin E.

7. The effervescent tablet, powder or granule of claim 5, wherein said one or more minerals is selected from the group consisting of manganese, selenium, calcium and magnesium.

8. The effervescent tablet, powder or granule of claim 5, wherein said one or more drugs is selected from the group consisting of phenylephrine, pseudoephedrine, chlorpheniramine maleate, aspirin, ibuprofen, naproxin, caffeine and acetaminophen.

9. The effervescent tablet, powder or granule of claim 5, wherein said one or more herbal ingredients is selected from the group consisting of ginkgo biloba, Echinacea, ginseng, ginger and St. John's wort.

10. The effervescent tablet, powder or granule of claim 1, further comprising one or more materials that improves the organoleptic properties of the tablet, powder or granule.

11. The effervescent tablet, powder or granule of claim 10, wherein said material that improves the organoleptic properties of the tablet, powder or granule is selected from the group consisting of flavors, colors, artificial sweeteners, and viscosity modifiers.

12. The effervescent tablet, powder or granule of claim 11, wherein said artificial sweetener is selected from the group consisting of saccharin, acesulfame-K, sucralose, cyclamate, aspartame, and sucralose.

13. The effervescent tablet, powder or granule of claim 11, wherein said viscosity modifiers are selected from the group consisting of gum Arabic, gum acacia, carboxy methyl cellulose and hydroxy propyl methyl cellulose.

14. The effervescent tablet, powder or granule of claim 1, further comprising a lubricant.

15. The effervescent tablet, powder or granule of claim 14, wherein said lubricant is selected from the group consisting of polyethylene glycol, magnesium stearate, stearic acid, sucrose stearate, sodium stearyl fumarate, various silicone oils, vegetable oils, mineral oils and sodium benzoate.

16. The effervescent tablet, powder or granule of claim 1, further comprising a binder.

17. The effervescent tablet, powder or granule of claim 16, wherein said binder is selected from the group consisting of sorbitol, microcrystalline cellulose, dicalcium phosphate, maltodextrin, corn syrup solids, dextrose, sucrose, polyvinyl alcohol, polyvinyl pyrrolidone and sodium sulfate.

18. The effervescent tablet, powder or granule of claim 1, further comprising an electrolyte selected from the group consisting of ions of: sodium, potassium, chlorine, magnesium, calcium, bicarbonate, citrate, tartrate, malate and fumarate.

19. The effervescent tablet, powder or granule of claim 1, wherein the sodium content of said solution is 24 mmol/liter-52 mmol/liter.

20. The effervescent tablet, powder or granule of claim 1, wherein said chloride content of said solution is 25.5 mmol/liter-40 mmol/liter.

* * * * *